United States Patent
Ciomei et al.

(10) Patent No.: US 8,912,194 B2
(45) Date of Patent: *Dec. 16, 2014

(54) CDK INHIBITOR FOR THE TREATMENT OF MESOTHELIOMA

(75) Inventors: Marina Ciomei, Corsico (IT); Angela Scaburri, Legnano (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 677 days.

This patent is subject to a terminal disclaimer.

(21) Appl. No.: 13/130,903

(22) PCT Filed: Nov. 23, 2009

(86) PCT No.: PCT/EP2009/065643
§ 371 (c)(1),
(2), (4) Date: May 24, 2011

(87) PCT Pub. No.: WO2010/058006
PCT Pub. Date: May 27, 2010

(65) Prior Publication Data
US 2011/0224222 A1    Sep. 15, 2011

(30) Foreign Application Priority Data
Nov. 24, 2008  (EP) ................... 08169790

(51) Int. Cl.
*A61K 31/519*  (2006.01)
(52) U.S. Cl.
CPC .................. *A61K 31/519* (2013.01)
USPC .................................................. 514/252.16
(58) Field of Classification Search
CPC ........................... C07D 403/14; A61K 31/519
USPC ................ 514/49, 252.16; 544/371; 206/438
See application file for complete search history.

(56) References Cited

U.S. PATENT DOCUMENTS

| 8,518,930 B2 * | 8/2013 | Ciomei et al. ................. 514/185 |
| 2008/0146555 A1 | 6/2008 | Caligiuri et al. |
| 2011/0190311 A1 * | 8/2011 | Ciomei et al. ............ 514/252.16 |

FOREIGN PATENT DOCUMENTS

| JP | 2006-508185 | 3/2006 |
| WO | WO 03/039536 A1 | 5/2003 |
| WO | WO 2004/041267 A1 | 5/2004 |
| WO | WO 2004/104007 * | 12/2004 ........... C07D 487/04 |
| WO | WO 2004/104007 A1 | 12/2004 |
| WO | WO 2007/090794 A1 | 8/2007 |
| WO | 2010/012777 A1 | 2/2010 |

OTHER PUBLICATIONS

Ceresoli G.L. et al., "Phase II Study of Pemetrexed Plus Carboplatin in Malignant Pleural Mesothelioma", *Journal of Clinical Oncology* 24(9):1443-1448 (Mar. 20, 2006), XP008118182.
Hirao T. et al., "Alternations of the p16$^{INK4}$ Locus in Human Malignant Mesothelial Tumors", *Carcinogenesis* 23(7):1127-1130 (2002).
Whitson B.A. et al., "Molecular Pathways in Malignant Pleural Mesothelioma", *Cancer Letters* 239:183-189 (2006).
Kobayashi N. et al., "Frequent p16 Inactivation by Homozygous Deletion or Methylation is Associated with a Poor Prognosis in Japanese Patients with Pleural Mesothelioma", *Lung Cancer* 62:120-125 (2008).
Davidson B. et al., "Expression of the Nerve Growth Factor Receptors TrkA and p75 in Malignant Mesothelioma", *Lung Cancer* 44:159-165 (2004).
Scagliotti G.V. et al., "Phase II Study of Pemetrexed With and Without Folic Acid and Vitamin $B_{12}$ as Front-Line Therapy in Malignant Pleural Mesothelioma", *Journal of Clinical Oncology* 21(8):1556-1561 (Apr. 15, 2003).
Castagneto B. et al., "Phase II Study of Pemetrexed in Combination With Carboplatin in Patients With Malignant Pleural Mesothelioma (MPM)", *Annals of Onology* 19(2):370-373 (Feb. 2008).
Zucali P.A., "Gemcitabine and Vinorelbine in Pemetrexed-Pretreated Patients With Malignant Pleural Mesothelioma", *Cancer* 112(7):1555-1561 (Apr. 1, 2008).
International Search Report dated Mar. 8, 2010 from the European Patent Office from related International Application No. PCT/EP2009/065643.
Nguyen D.M. et al., "Abrogation of p21 Expression by Flavopiridol Enhances Depsipeptide-Mediated Apoptosis in Maligant Pleural Mesothelioma Cells", Clinical Cancer Research 10:1813-1825 (Mar. 1, 2004).
Richard C. et al., "Flavopiridol Sensitivity of Cancer Cells Isolated from Ascites and Pleural Fluids", Clinical Cancer Research 11(9):3523-3529 (May 1, 2005).
European Communication under Rule 71(3) dated Jan. 31, 2013 received from related Application No. 09 760 831.9.

* cited by examiner

*Primary Examiner* — Erich A Leeser
(74) *Attorney, Agent, or Firm* — Scully, Scott, Murphy & Presser, P.C.

(57) ABSTRACT

The invention provides a low molecular weight ATP-competitive CDK inhibitor for use in the treatment of mesothelioma. The compound can be administered together with one or more cytotoxic or cytostatic agents.

1 Claim, 2 Drawing Sheets

CDK INHIBITOR FOR THE TREATMENT OF MESOTHELIOMA

TECHNICAL FIELD

The present invention relates to the treatment of mesothelioma patients through the use of a low molecular weight ATP-competitive CDK (Cyclin-Dependent Kinase) inhibitor.

BACKGROUND ART

Malignant mesothelioma is a locally invasive and rapidly fatal neoplastic disease, linked to asbestos exposure.

There are many genetic defects that contribute to the outcome of mesothelioma. Homozygous deletion of p16/CDKN2A (cyclin-dependent kinase inhibitor 2A) is found in approximately 75% of mesotheliomas and may be the most common genetic alteration in this cancer [Hirao T, Bueno R, Chen C J, Gordon G J, Heilig E, Kelsey K T. Carcinogenesis 2002; 23(7):1127-1130; Whitson B A, Kratzke R A. Cancer Lett 2006; 239(2):183-189]. In terms of prognosis, p16/CDKN2A loss is associated with a more aggressive clinical behavior of mesotheliomas [Kobayashi N, Toyooka S, Yanai H, Soh J, Fujimoto N, Yamamoto H, et al. Lung Cancer 2008 62(1):120-5; Davidson B, Reich R, Lazarovici P, Florenes V A, Risberg B, Nielsen S, Lung Cancer 2004; 44(2):159-165.].

The p16 protein leads to cell cycle arrest in the G1 phase by inhibiting cyclin dependent kinase. As a consequence of the lack of p16/CDKN2A, the G1 to S checkpoint control is lost, resulting in a hyperphosphorylation of the tumor suppressor Retinoblastoma (pRb) and cell progression to S phase.

In addition, also the Thropomyosin Receptor Kinase A (TRKA) plays a significant role in the biology of this disease. In fact, frequent expression of activated TRKA (P-TRKA) is frequently found in malignant mesothelioma and is predominantly seen in effusions and in peritoneal lesions, tumors that appear in younger patients [Whitson B A, Kratzke R A. Molecular pathways in malignant pleural mesothelioma. Cancer Lett 2006; 239(2):183-189].

The incidence of mesothelioma worldwide is increasing and only a minority of patients can benefit from a surgical resection. For patients who are not amenable to curative resection, median overall survival is around 6-7 months. Therapeutic options are limited. Most patients, either treated or untreated, die of complications from local disease. Marketed chemotherapeutic agents, as a single agent or in combination, did not prove able to significantly impact survival.

Current therapeutic options include the use of pemetrexed (marketed under the trademark ALIMTA®) as a single agent, that has demonstrated a moderate response rate of 14.1% and a median overall survival of 10.7 months [Scagliotti G V, Shin D M, Kindler H L, Vasconcelles M J, Keppler U, Manegold C, et al. J Clin Oncol 2003; 21(8):1556-1561] or combinations with platinum derivatives (cisplatin or carboplatin) plus pemetrexed [Castagneto B, Botta M, Aitini E, Spigno F, Degiovanni D, Alabiso O, et al. Ann Oncol 2008; 19:370-373].

There are no approved agents for second-line treatment of mesothelioma. Chemotherapy options are limited and include gemcitabine, vinorelbine and other antifolate compounds [Zucali P A, Ceresoli G L, Garassino I, De Vincenzo F, Cavina R, Campagnoli E Cancer 2008; 112(7):1555-1561].

Indeed, there is a very high unmet medical need for new potent agents for the treatment of mesotheliomas. The present invention addresses this problem.

SUMMARY OF THE INVENTION

The invention provides a low molecular weight compound able to inhibit two of the main pathways involved in mesothelioma pathogenesis through inhibition of CDKs and of tyrosine kinase growth factor receptor-mediated signalling pathways and efficacious in inhibiting mesothelioma proliferation.

The compound of the present invention showing the desired activity is a pyrazoloquinazoline designed to target the ATP pocket of protein kinases. The compound has revealed to be a potent ATP-competitive inhibitor of CDKs. The compound has been found to display a significant inhibitory potency towards TRKA.

In view of its biological activity, the compound of the invention offers a new path for the development of a treatment for the patient population suffering from mesothelioma.

DETAILED DESCRIPTION OF THE INVENTION

Figure 1:
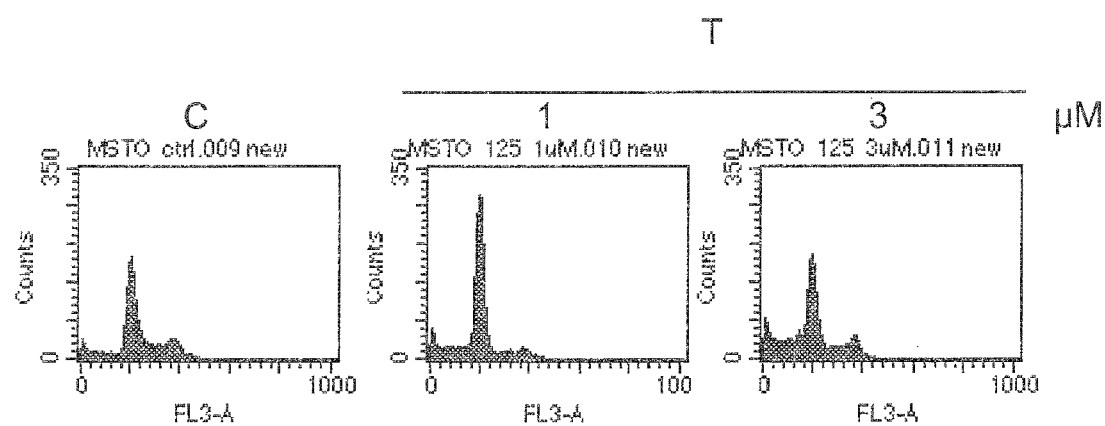
FIG. 1 illustrates the cytofluorimetric profile of untreated cells (C) and of cells treated with two doses (1 and 3 μM) of the compound of formula (I) (T), to evaluate the effect on cell cycle progression and induction of apoptosis on MSTO-211H cell line.

In a first aspect, the present invention relates to a compound of formula (I)

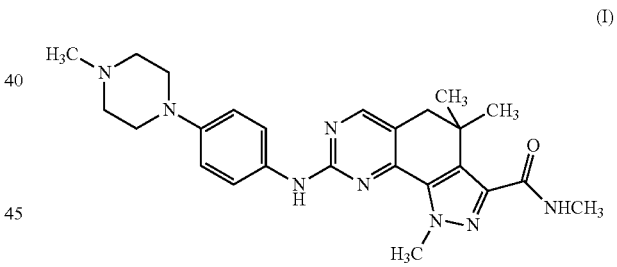

(I)

or a pharmaceutically acceptable salt thereof for use in a method for treating a mesothelioma.

As used herein the term "mesothelioma" includes pleural, peritoneal and pericardial mesotheliomas and all the histological categories: epithelioid, sarcomatoid and mixed/biphasic.

The compound of formula (I) has the chemical name 8-[4-(4-methyl-piperazin-1-yl)-phenylamino]-1,4,4-trimethyl-4,5-dihydro-1H-pyrazolo[4,3-h]quinazoline-3-carboxylic acid methylamide. It can be prepared as described in WO2004104007, is endowed with protein kinase inhibitory activity and is thus useful in therapy as antitumor agent. In particular, the preferred preparation of the compound of formula (I) is that described in example 58 of the above mentioned International Patent Application.

Pharmaceutically acceptable salts of the compound of formula (I) include the acid addition salts with inorganic or organic acids, e.g., nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid and the like.

Within the scope of the claimed invention is the use of all the possible isomers and their admixtures and of both the metabolites and the pharmaceutically acceptable bio-precursors (otherwise referred to as pro-drugs) of the compounds of formula (I). Prodrugs are any covalently bonded compounds, which release the active parent drug, according to formula (I), in vivo.

A therapeutically effective amount of the compound according to formula (I) may be administered to a subject upon determination of the subject as having a disease or unwanted condition that would benefit by treatment with said compound. Medical or clinical personnel may make the determination as part of a diagnosis of a disease or condition in a subject. The compound may also be used in the prevention of such conditions, which may be viewed as reducing the probability of a subject having one or more of the conditions.

As used herein, a "therapeutically effective amount" of a compound refers to an amount sufficient to achieve its intended purpose. Determination of the effective amounts is well within the capability of those skilled in the art based upon the achievement of a desired effect. An effective amount will depend on factors including, but not limited to, the size of a subject and/or the degree to which the disease or unwanted condition from which a subject suffers has progressed. The effective amount will also depend on whether the compound is administered to the subject in a single dosage or periodically over time.

The compound of formula (I) of the present invention is intended for the treatment of subjects. As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs and cats; laboratory animals including rodents, such as rats, mice and guinea pigs, and the like. Examples of non-mammals include, but are not limited to, birds, fish and the like.

The term "treating" as used herein includes achieving a therapeutic benefit. By therapeutic benefit is meant eradication or amelioration of the underlying disorder being treated. For example, in a cancer patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder.

Another object of the present invention is a therapeutic combination comprising (a) the compound of formula (I) as defined above and (b) one or more cytotoxic or cytostatic chemical agents, for use in a method for treating a malignant mesothelioma.

Exemplary cytostatic or cytotoxic chemical agents includes alkylating agents, alkylating-like agents (i.e. Platinum derivatives, such as Cisplatin and Carboplatin), antimetabolite agents (e.g. pemetrexed), antimicrotubules agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

In a particularly preferred embodiment the present invention provides a therapeutic combination comprising the compound of formula (I) as defined above, a Platinum derivative and pemetrexed, for use in a method for treating a malignant mesothelioma.

The present invention also relates to a pharmaceutical composition comprising a compound of formula (I) as defined above admixed with a pharmaceutically acceptable carrier, diluent or excipient, for use in the treatment of malignant mesotheliomas.

In a further embodiment the pharmaceutical composition according to the invention further comprises one or more cytotoxic or cytostatic chemical agents.

In a particularly preferred embodiment, the present invention provides a pharmaceutical composition comprising a compound of formula (I) as defined above, a Platinum derivative and pemetrexed, for use in a method for treating a malignant mesothelioma.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose, saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine, methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions or suspensions.

As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol.

In therapeutic use, the compound of formula (I) is administered to a subject at dosage levels of from about 10 mg/m$^2$ to about 400 mg/m$^2$ of body surface per day. A dosage level of from about 20 mg/m$^2$ to 200 mg/m$^2$ constitutes a particularly suitable range. For an adult human subject, a dosage of from about 20 mg to about 800 mg per dose, more preferably from about 40 mg to about 400 mg per dose, from 1 to 28 consecutive days, may be used as a non-limiting example. A preferred schedule of treatment consists of a dose of 150 mg/day for seven days of treatment followed by seven days of rest in a two-week cycle. Cycles can be repeated as long as requested to control the diseases.

Lower or higher doses than those disclosed herein may be used, as required. Such dosages, however, may be altered depending on a number of variables, not limited to the activity of the compound used, the condition to be treated, the mode of administration, the regimen of treatment, the requirements of the individual subject, the severity of the condition being treated and the judgment of the practitioner. The foregoing ranges are merely suggestive, as the number of variables in regard to an individual treatment regime is large and considerable excursions from these recommended values are not uncommon.

With the aim to better illustrate the present invention, without posing any limitation to it, the following examples are now given.

EXAMPLES

Example 1

Scintillation Proximity Assay (SPA) Format for Kinases

This assay allows measurement of the inhibition of the kinase activity of a specific enzyme obtained with test compound. Different kinases can be tested in parallel.

A biotinylated substrate is trans-phosphorylated by a specific kinase in the presence of ATP including a γ33-ATP tracer. At the end of the reaction the phosphorylated substrate is then captured using Streptavidin-coated SPA beads. A dense 5M CsCl solution is added and the mixture is incubated for four hours. This causes the SPA beads to float to the top of the CsCl solution containing the unincorporated radiolabelled ATP.

The extent of phosphorylation is measured using a β-counter. In these assays, the compound of formula (I) showed a potent inhibitory activity on the CDK2/Cyclin A complex ($IC_{50}$=45 nM), showing activity also towards closely related CDKs, i.e. CDK1, CDK4, and CDK5 (1050=398, 160 and 265 nM, respectively), but also towards Thropomyosin Receptor Kinase A (TRKA) (1050=53 nM).

Example 2

Effect of Compound of Formula (I) in Mesothelioma Cells In Vitro

MSTO-211H, NCI-H2052 and NCI-H28 mesothelioma cell lines were cultured in RPMI 1640 added with 10% FCS, 2 mM glutamine, 1 mM sodium pyruvate and 10 mM HEPES. For all the experiments cells were seeded at the density of $1 \times 10^4/cm^2$, the day after treatment with the compound for the prescribed duration and then collected at the reported times. Inhibition of Cell Proliferation.

Cells were washed and counted 72 hours after the treatment. Cell proliferation was determined by a cellular adenosine triphosphate monitoring system. Cell proliferation was compared to control cells. The concentration inhibiting cell proliferation by 50% ($IC_{50}$) was calculated.
Analysis of Cell Cycle Progression and Apoptosis Induction Cells were washed 24 hours after the treatment, fixed with cold methanol 70% and stored at −20° C. Fixed cells were washed with PBS to remove methanol and were stained with 25 μg/mL of propidium iodide, 5 μg/mL of RNase, and 0.125 μg/mL of Nonidet P 40. Cells were kept at room temperature for 60 minutes in the dark and were analyzed by BD FACS-Calibur™ system interfaced to a Macintosh G4 computer with BD CellQuest™ 3.3 software. All doublets or aggregates were removed during analysis by an appropriate gate on an FL3-A/FL3-W dot plot and DNA content analysis was performed in ≥10,000 gated cells. DNA histograms (shown in FIG. 1) were analyzed using ModFit LT™

As shown in FIG. 1, as example, cell cycle progression is affected by the compound of formula (I) resulting in a G1 block evident in cells treated with 1 μM and increase of the sub G1 peak (induction of apoptosis) in cells treated with 3 μM.

The results of these assays are also reported in Table 1. The compound of formula (I) is active on all the tested mesothelioma cells (first column): it is able to inhibit proliferation with an $IC_{50}$ in the range 0.23-1.56 μM (second column) and it is able to induce apoptosis as measured by cytofluorimetric analysis of percentage of cells with a sub G1 DNA content (third column).

TABLE 1

| Mesothelioma cell line | $IC_{50}$ (μM) | Sub G1 % |
|---|---|---|
| MSTO-211H | 0.23 ± 0.10 | 24 |
| NCI-H2052 | 0.74 ± 0.37 | 14 |
| NCI-H28 | 1.56 ± 0.52 | 5 |

Example 3

Evaluation of Compound of Formula (I) Mode of Action by Western Blot Analysis

Treated cells were lysed by adding SDS sample buffer (0.125M Tris-HCl pH6.8, 5% SDS). Samples were heated to 95° C. for 5 minutes and then sonicated using an Ultrasonic 2000 ARTEK. Lysed cells were centrifuged at 13,000 RPM for 10 minutes. Protein quantification was determined using BCA buffer (Pierce) and a BSA standard curve. 20 μg protein extract per well were loaded and separated by SDS-PAGE gel 7.5-10% (PAGE-PLUS 40% concentrate AMRESCO). The gel was blotted onto nitrocellulose filters (Hybond Amersham) in a buffer containing 25 mM Tris HCl pH 8.3, 192 mM Glycine and 20% methanol. The filters were saturated in 5% low-fat milk in TBS containing 0.1% Tween 20 (TBS-T) for 2 hours at room temperature and than incubated overnight at 4° C. with the primary monoclonal followed by washes in TBS-T and incubation using a secondary anti mouse antibody. The bands were visualized using the "Super Signal West Pico" Pierce.

The results obtained in all the tested cell lines showed that the compound of formula (I) is able to interfere with both the main pathways involved in mesothelioma pathogenesis.

Figure 2:
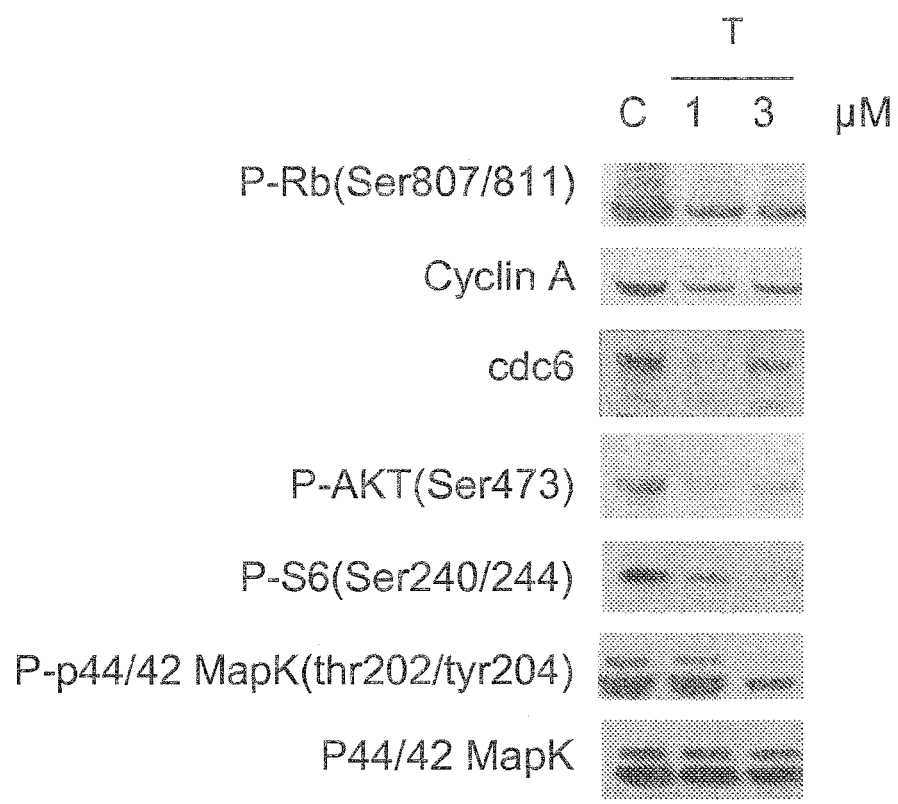
FIG. 2 illustrates protein expression in untreated cells (C) and in cells treated with two doses (1 and 3 μM) of the compound of formula (I) (T). The amount of phosphorylated Rb protein (the direct substrate of CDK2), the amount of Cyclin A and cdc6 (proteins involved in the control of cell cycle progression) and the amount of phosphorylated AKT; phosphorylated S6; phosphorylated p44/42MAPK and total p44/42MAPK was evaluated and shown.

A decrease in the cell cycle related markers is observed in all mesothelioma cell lines tested. FIG. 2, as example, shows the results obtained with two doses of compound of formula (I) in NCI-H28 cells (mutated in p16/CDKN2A) treated for 24 hours. A strong inhibition of Rb phosphorylation as well as of cyclin A and cdc6 expression is evident.

The ability of compound of formula (I) to inhibit also the pathways mediated by tyrosine kinase growth factor receptors was also evaluated. Inhibition in phosphorylation of AKT; S6 and MAPK is also reported in FIG. 2 in NCI-H28 cells.

The invention claimed is:
1. A method of treating a malignant mesothelioma comprising administration of a compound of formula (I)

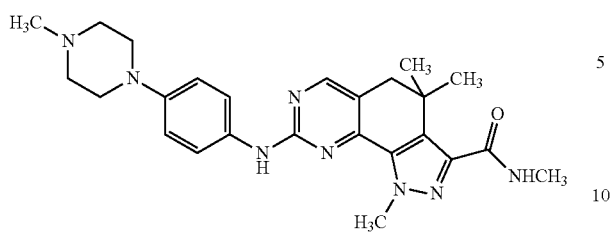
or a pharmaceutically acceptable salt thereof and administration of one or more cytotoxic or cytostatic chemical agents selected from the group consisting of pemetrexed and a platinum derivative.